United States Patent [19]
Dextradeur et al.

[11] Patent Number: 5,976,188
[45] Date of Patent: Nov. 2, 1999

[54] MODULAR PROSTHESIS SYSTEM WITH HYBRID FIXATION

[75] Inventors: Alan J. Dextradeur, Franklin; Mark A. Manasas, Easton; Peter T. Bianco, Wellesley, all of Mass.

[73] Assignee: Johnson & Johnson Professional, Inc., Raynham, Mass.

[21] Appl. No.: 08/955,141

[22] Filed: Oct. 21, 1997

[51] Int. Cl.[6] ............................. A61F 2/30; A61F 2/28; A61F 2/02; A61F 2/32

[52] U.S. Cl. ............................. 623/18; 623/16; 623/11; 623/22; 623/23

[58] Field of Search ................................. 623/23, 21, 18, 623/19, 16, 36, 37, 22

[56] References Cited

U.S. PATENT DOCUMENTS

| | | | |
|---|---|---|---|
| 4,878,917 | 11/1989 | Kranz et al. | 623/18 |
| 5,035,712 | 7/1991 | Hoofman | 623/23 |
| 5,133,772 | 7/1992 | Hack et al. | 623/23 |
| 5,156,627 | 10/1992 | Amstutz et al. | 623/23 |
| 5,201,771 | 4/1993 | Belykh et al. | 623/23 |
| 5,343,877 | 9/1994 | Park | 128/898 |
| 5,597,383 | 1/1997 | Carbone | 623/23 |
| 5,607,431 | 3/1997 | Dudasik et al. | 606/80 |
| 5,858,020 | 1/1999 | Johnson et al. | 623/23 |
| 5,876,459 | 3/1999 | Powell | 623/18 |

FOREIGN PATENT DOCUMENTS

| | | | |
|---|---|---|---|
| 2 662 913 A1 | 12/1991 | France | 623/23 |

OTHER PUBLICATIONS

Brochure entitled Bridge Total Hip System, © Wright Medical Technology, Inc., Arlington, TN, 1994.

Article entitled Fit of the Uncemented Femoral Component and the Use of Cement Influence the Strain Transfer to the Femoral Cortex, *Journal of Orthopaedic Research*, © 1994 Orthopaedic Research Society, Murali Jasty, Daniel O. O'Connor, Robert M. Henshaw, Timothy P. Harrigan, and William H. Harris.

Article entitled Loosening of the Femoral Component after Use of the Medullary–Plug Cementing Technique, © 1986 *The Journal of Bone and Joint Surgery, Incorporated*, William H. Harris, M.D. and William A. McGann, M.D.

Article entitled The Effect of Improved Cementing Techniques on Component Loosening in Total Hip Replacement, An 11–Year Radiographic Review, From Massachusetts General Hospital and Harvard Medical School, Boston, *The Journal of Bone and Joint Surgery*, vol. 72–B, No. 5, Sep. 1990.

Article entitled Hybrid Fixation Modular Tibial Prosthesis, Early Clinical and Radiographic Results and Retrieval Analysis, *The Journal of Arthroplasty* vol. 10 No. 4 1995, James A. Shaw, MD.

Brochure entitled The S–ROM® Total Hip System—Cementless Modular Femoral prothesis (Fluted Stem with proximal Sleeve) Surgical Reference Guide Wall Chart, Johnson & Johnson orthopaedics, © 1995 Joint Medical Products Corporation.

Brochure entitled The S–ROM Total Hip System—Cementless Femoral prosthesis (Fluted Stem with ZT™ Proximal Sleeve) Surgical Procedure, Johnson & Johnson Orthopaedics, Joint Medical Products Corporation ©1994.

*Primary Examiner*—Mickey Yu
*Assistant Examiner*—Alvin Stewart
*Attorney, Agent, or Firm*—Nutter, McClennen & Fish, LLP

[57] ABSTRACT

A modular system for hybrid fixation of a joint prosthesis into a bone cavity includes a sleeve having a bore therethrough. The sleeve is cementable within the bone cavity. A prosthetic component is insertable into the bore of the sleeve. The prosthetic component is retained within the sleeve and secured to the bone without cement.

23 Claims, 3 Drawing Sheets

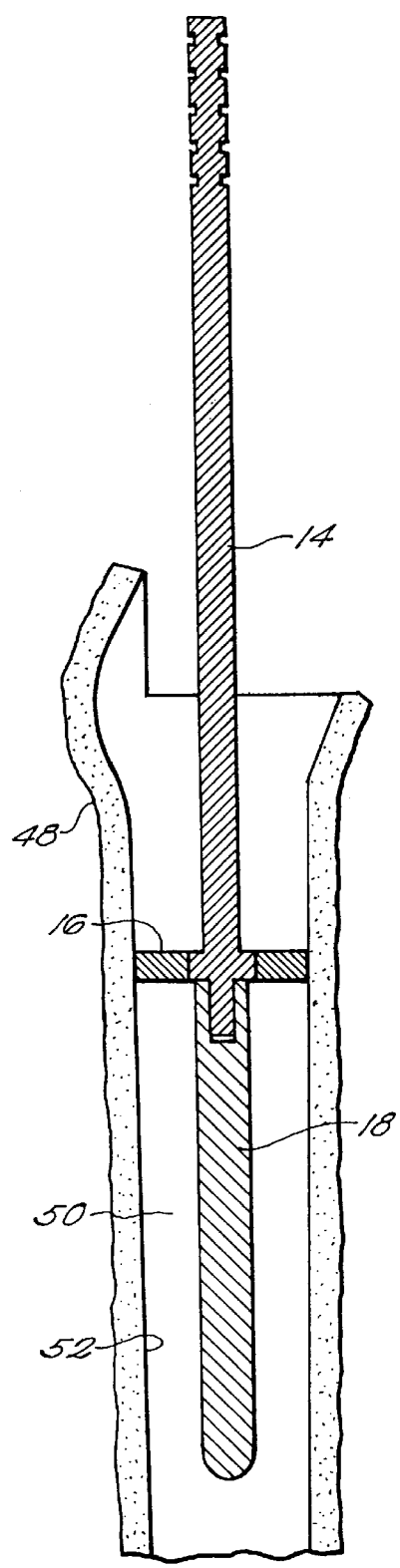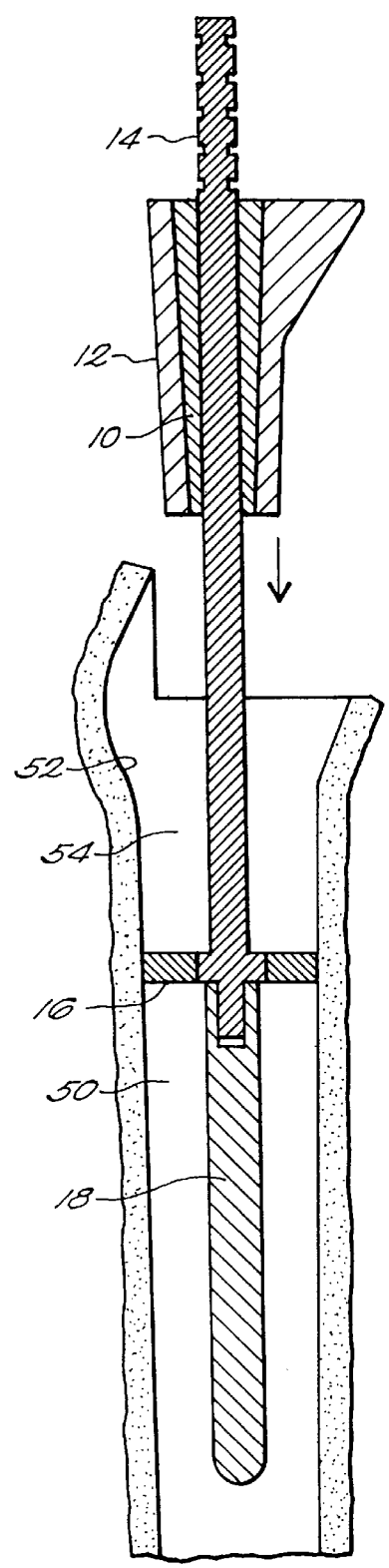
*FIG. 2*  *FIG. 3*

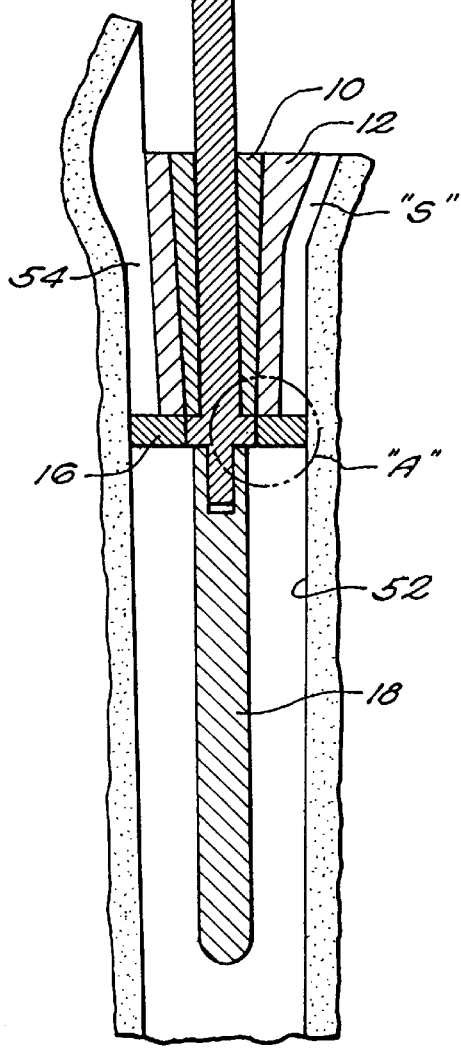
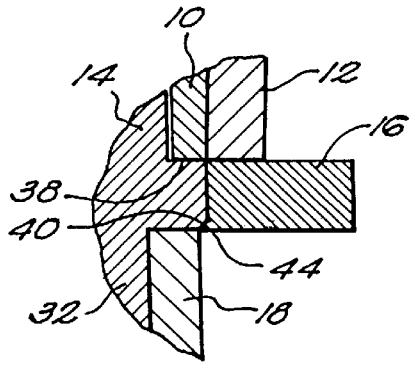
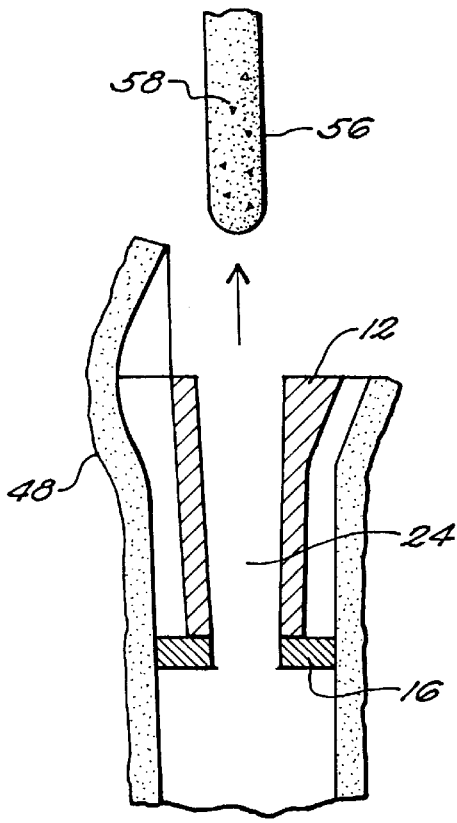
FIG. 4  FIG. 5  FIG. 6

MODULAR PROSTHESIS SYSTEM WITH HYBRID FIXATION

CROSS REFERENCE TO RELATED APPLICATIONS

Not applicable.

STATEMENT REGARDING FEDERALLY SPONSORED RESEARCH

Not applicable.

BACKGROUND OF THE INVENTION

Disease and/or trauma cause deterioration of natural joints of the human body. Replacement of natural joints with joint prostheses can distinctly enhance the quality of life of an individual affected by such joint conditions. Various joint prostheses are known. Among the more common joint prostheses are those that replace all or part of the natural knee and hip joints.

Components of joint prostheses must be implanted and secured within existing bone. In the case of hip arthroplasty, a surgical technique in which the hip joint is replaced by a prosthetic joint, a cavity is prepared in a proximal portion of the patient's femur to receive a femoral stem, a portion of a prosthetic hip joint. Other joint replacement surgical techniques require the formation of similar cavities within existing bone for the installation of various prosthesis components.

Once such a cavity is prepared, the prosthesis component may be secured within the cavity by a number of techniques. For example, the prosthesis component may be cemented within the cavity, or it can be installed through mechanical fixation by a friction fit or the use of a fixation device.

Yet another technique, known as "hybrid fixation," uses cement to secure a portion of a component in place, whereas other portions of the component are secured by directly mating with the bone or other methods of securement. This technique can be particularly challenging, however, as cement must be confined to a selected portion of the component, avoiding the non-cemented surfaces, yet be applied in sufficient abundance to create a void-free cement mantle. The difficulty is even greater when the portion to be cemented is bounded by non-cemented surfaces.

Although techniques exist to combine cement-based and cement-free fixation of bone prosthesis components within bone, it is desirable to provide additional techniques that can be easily implemented and that address the challenges presented by hybrid fixation.

SUMMARY OF THE INVENTION

The present invention addresses problems associated with hybrid fixation by providing a modular joint prosthesis system that can include a first portion to be cemented and a second portion that is adapted for cementless fixation, wherein the first and second portions can be mated. The system can include structures for positioning the first and second portions and for localizing or creating one or more boundaries to inhibit cement flow or migration.

In an exemplary embodiment, structures are provided to position a sleeve having a bore therethrough at a selected location within a bone canal where the sleeve can be cemented into place. The bore of the sleeve is dimensioned to receive a prosthetic component that is not secured by cement to the bone or to the sleeve.

The prosthetic joint system can include a sleeve having a bore extending therethrough, and a plug having a channel extending therethrough, wherein the plug is dimensioned to be slidably received within the bore of the sleeve.

The system can further include a guide that is slidably receivable within the channel of the plug, a seal that is positionable with the guide, and a pilot shaft engageable with the guide.

BRIEF DESCRIPTION OF THE DRAWINGS

Other features and benefits of the invention can be more clearly understood with reference to the specification and the accompanying drawings in which:

FIGS. 2–6 depict steps of a surgical procedure using the prosthesis system illustrated in FIG. 1.

DETAILED DESCRIPTION OF THE INVENTION

Figure 1:
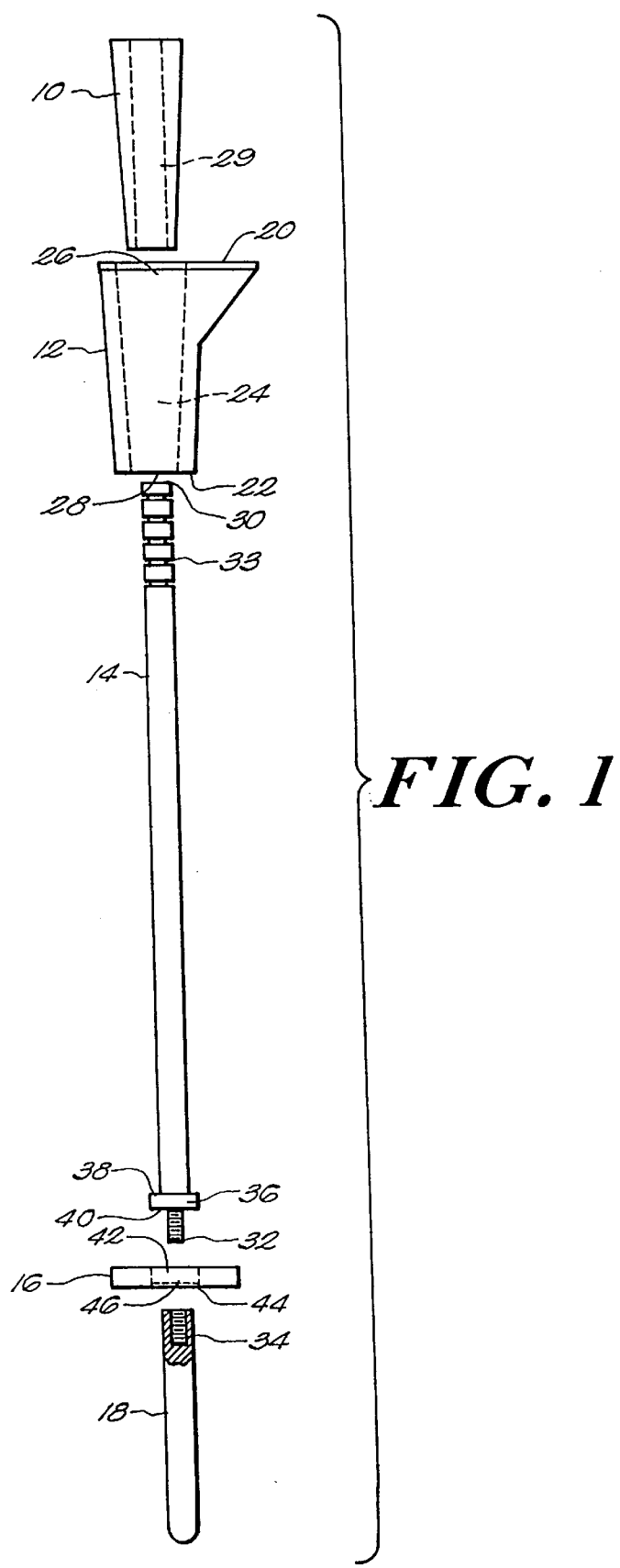
FIG. 1 is an exploded view of a modular prosthesis system of the invention.

FIG. 1 is an exploded view of a system in accordance with the invention that includes a plug 10, a sleeve 12, a guide 14, a seal 16, and a pilot shaft 18.

The sleeve 12 is a body having a first end 20 and a second end 22. A bore 24 is defined by the body, and the bore is accessible through a first opening 26 at the first end 20 of the body and through a second opening 28 at the second end 22 of the body. The bore 24 is dimensioned to receive the plug 10 therein, and the sleeve 12 is dimensioned to be received within a prepared bone cavity, e.g., a femoral bone canal, as shown in subsequent figures. The bore 24 in the sleeve 12 is dimensioned to receive another prosthetic component as described below when the plug 10 is not within the bore. Both the bore 24 in the sleeve 12 and the plug 10 can be tapered, or frustroconical, as shown in FIG. 1.

The sleeve 12 can be provided with any desired shape compatible with the structural requirements of other prosthetic components to which it can be mated. For example, the sleeve 12 can be configured to distribute stress and/or transfer strain to a portion of a bone into which it has been implanted. The embodiment of the sleeve 12 shown in FIG. 1 has a generally triangular shape, wherein the circumference of the sleeve near the first end 20 is greater than at the second end 22. The sleeve can be made of titanium, cobalt-chrome, ceramic, or other biologically compatible materials. Also, the exterior surface of the sleeve can be textured to promote bonding with bone cement deposited around the sleeve, as described below.

The plug 10, which is removably insertable into the bore 24 of the sleeve 12, defines a channel 29 capable of slidable engagement with the guide 14. The plug 10 is capable of completely or partially fining the bore 24 of the sleeve 12. In an exemplary embodiment, the plug 10 is made of a medical-grade plastic. However, the plug material is not of particular importance.

The guide 14 is a tool useful for inserting, guiding, positioning, and removing system components during surgical procedures, as described below. In the illustrated embodiment, the guide 14 is an elongate rod having a first end 30 and a second end 32. The guide 14 can be provided with grasping aids and measurement indicia. For example, the illustrated embodiment of the guide 14 includes evenly spaced-apart circumferential grooves 33 near the first end 30 of the guide. The grooves provided a textured surface that is easily grasped with a moist surgical glove or grasping tool, as well as longitudinal measurement indicia.

The guide 14 can also include one or more structures that are useful to selectively engage and/or position other system elements. For example, the second end 32 of the guide 14 can be configured to selectively engage the pilot shaft 18. In the illustrated embodiment, the second end 32 of the guide 14 is threaded so as to be able to engage a cooperatively threaded structure 34 defined by the pilot shaft 18 when the guide is rotated with respect to the pilot shaft. The guide 14 can further include a feature, such as an abutment structure 36, that is useful for pushing and/or pulling other structures into selected positions, as will be described below. The abutment structure includes a first abutment surface 38 and a second abutment surface 40.

The seal 16, which is positionable using the guide 14, is a body having dimensions that enable it to substantially or completely occlude a portion of, or all of, a cavity or passage, such as a reamed femoral canal, into which it is introduced. The seal 16 can have dimensions, structural features, surface features, and material characteristics that cause the seal to bind with or engage surfaces defining the cavity or passage, to cause the seal to remain in the selected location.

In an exemplary embodiment, the seal 16, generally disk or torus shaped, defines an aperture 42 through which the second end 32 of the guide 14 is extendible to engage the pilot shaft 18. A shoulder 44, shown in greater detail in FIG. 5, is defined by a reduced diameter region of the aperture 42, and engages (by abutment) the second abutment surface 40 of the guide 14. A second aperture 46, defined by the shoulder, has a diameter of sufficient dimension to permit the pilot shaft and other similarly dimensioned structures to move bi-directionally through the second aperture. In the illustrated embodiment, the first aperture 42 has a greater diameter than the second aperture 46.

The seal 16 can be rigid, flexible, or partially rigid with a peripheral and/or central flexible, deformable, or compressible region. In an exemplary embodiment, the seal 16 is made of polymethylmethacrylate (PMMA). Other biocompatible materials are also suitable.

The pilot shaft 18, although useful for centering components within a bone canal and for verifying adequate canal depth, is not a required element of the system. The guide 14 alone can be used to position the seal 16. In the illustrated embodiment, the pilot shaft 18 has a maximum diameter that is less than the diameter of the second aperture 46. Thus, other objects, such as prosthetic components, that are dimensionally similar to the pilot shaft 18 can be passed through the apertures in the seal 16.

In order to accommodate a wide range of patient requirements, a surgical kit in accordance with the invention can include a selection of different size and shape guides, sleeves, plugs, seals, and pilot shafts, having the features described herein to allow a surgeon to mix-and-match as desired.

Turning now to FIGS. 2–6, additional details of the system of the invention are described in association with a description of an exemplary surgical procedure.

FIG. 2 depicts a femur 48 that has been cut and reamed in a manner known to those skilled in the art to prepare for implantation of a femoral prosthesis. Features of the femur 48 of particular interest in the subsequent description are the reamed femoral canal 50 and the canal wall 52.

Continuing to refer to FIG. 2, the guide 14 is shown mated to a selected pilot shaft 18, and the guide is in an abutting relationship with the seal 16. The guide 14 and the pilot shaft 18 are substantially aligned with and on the longitudinal axis of the femoral canal 50. However, off-axis placement is possible if desired. The seal 16 is positioned at a selected depth within the femoral canal 50, and the periphery of the seal contacts the canal wall 52 in a manner that occludes the femoral canal.

FIG. 3 illustrates a subsequent procedural step, wherein bone cement, such as PMMA, is deposited into a cavity 54 defined by the seal 16 and the canal wall 52 using techniques known to those skilled in the art. The seal 16 prevents all, or substantially all of the bone cement from migrating beyond the seal into the area of the femoral canal 50 occupied by the pilot shaft 18. Additionally, the seal 16 provides protection against particulate debris intrusion beyond the seal, thereby reducing the risk of complications associated with particulate debris, i.e., osteolysis.

The plug 10 and sleeve 12 are shown in a mated condition, wherein ends of the plug are flush with the ends of the sleeve. It is not a requirement that the proximal end of the plug be flush with the proximal end of the sleeve. Therefore, in other embodiments, the proximal end of the plug is below or above the proximal end of the sleeve.

The guide 14 is slidably engaged with the mated plug/sleeve assembly and slid into the cement filled cavity 54 in the direction indicated by the arrow. This technique promotes pressurization and ensures that the cavity 54 is completely filled with cement to reduce voids at the interface between the sleeve 12 and the cement.

FIG. 4 illustrates the plug/sleeve assembly within the cement filled cavity 54 in an abutting relationship with the seal 16. In an alternative procedure, the plug/sleeve assembly is slid into abutment with the seal 16 before cement is deposited into the cavity 54. Regardless of when and how cement and the plug/sleeve assembly are placed into the cavity 54, it should be noted that the plug 10 prevents cement from entering the bore 24 in the sleeve 12. As the cement hardens, the sleeve 12 is fixed in place.

The thickness of the seal 16 can be selected to adjust the longitudinal positioning of the sleeve 12 in relation to the canal wall 52, while keeping the bottom face of the seal at a selected point within the femur 48. This allows for the thickness of the cement to be controlled. For example, a seal 10 mm thick would create a larger space "S" between the seal 16 and the canal wall 52 than would a seal 5 mm thick in the region where the sleeve 12 overhangs bone. Although, the thickness of the seal 16 has a greater effect on the thickness of the cement mantle at region S, the entire cement mantle thickness is affected by the thickness of the seal.

FIG. 5 depicts the region identified as "A" in FIG. 4 in greater detail. In this view the exemplary structure of the second abutment surface 40 of the guide 14 and the shoulder 44 of the seal 16 are more readily apparent. It should be noted that the first abutment surface 38 of the guide 14 is aligned with the plug 10, but not with the sleeve 12. Thus, moving the first abutment surface 38 toward the plug 10, such as by pulling the guide 14, will cause the plug 10 to be extracted from the sleeve 12 without applying enough force to dislodge the cement secured sleeve from its selected location. Unless the pilot shaft 18 is disengaged from the guide 14, the pilot shaft 18, the guide 14, and the plug 10 can be removed from the sleeve 12 and the femur in a single step.

Although it may be desirable to wait until the cement has partially or completely hardened or cured before removing the guide 14, pilot shaft 18, and plug 10, these components can be removed immediately upon placing the sleeve 12 into the cavity 54, as the seal 16 can be sufficiently snug in the femoral canal to support the weight of the cement and the sleeve in addition to the seal itself. Applying light pressure to the first end 20 of the sleeve 12 while the guide 14, plug 10, and pilot shaft 18 are being extracted from the sleeve prevents the sleeve from being dislodged from the abutting relationship with the seal 16.

Referring now to FIG. 6, the guide 14, pilot shaft 18, and plug 10 have been withdrawn from the sleeve. Remaining in the femur 48 are the sleeve 12 and the seal 16. It should be noted that the bore 24 of the sleeve 12 is clear, free of cement, and capable of receiving another prosthetic component 56 that can be an element of the system, such as a femoral stem or a trial component. The resulting mating of sleeve 12 and prosthetic component 56 is cementless. In an exemplary system in accordance with the invention, the component 56 may have bone in/on-growth features 58, such as beads, a coating, or cavities and the like, as is known in the art. Alternatively, there may be clearance or a line to line fit between bone and implant surfaces. As the application and placement of cement has been carefully controlled, cement does not contact the surface 58 of the component 56, thereby degrading its mating performance. Additionally, if the prosthetic component 56 must be subsequently removed, it can be removed without the loss of diaphyseal bone which is intrinsic to the mantle of hardened cement. For example, if a periprosthetic fracture occurs distal to the sleeve 12, the component 56, such as a stem, can be removed without disturbing the cemented-in sleeve 12, and a longer stem can be inserted to bridge the fracture following any additional distal reaming which may be required.

The preceding description concerns hip arthroplasty. However, one of ordinary skill in the art will appreciate that other joint prostheses may benefit from the above described structures and techniques with suitable modification.

Although the invention has been shown and described with respect to exemplary embodiments thereof, various other changes, omissions and additions in form and detail thereof may be made therein without departing from the spirit and scope of the invention. All references noted herein are expressly incorporated by reference in their entirety.

What is claimed is:

1. A prosthetic joint system comprising:
   a sleeve having a first end, a second end, and a bore extending between the first and second ends;
   a plug having a first end, a second end, and a channel extending between the first and second ends, wherein the plug is dimensioned to be slidably received within the bore of the sleeve;
   a guide having a first end and a second end, wherein the guide is slidably receivable within the channel of the plug; and
   a prosthetic component adapted to be received in the bore of the sleeve so as to extend beyond the first and second ends of the sleeve.

2. The system of claim 1, wherein the plug is co-extensive with the bore of the sleeve.

3. The system of claim 2, wherein the guide includes inscribed indicia between the first end and the second end of the guide.

4. The system of claim 3, wherein the inscribed indicia include a plurality of spaced-apart, circumferential grooves.

5. The system of claim 4, wherein the plurality of spaced-apart, circumferential grooves are evenly spaced.

6. The system of claim 1, wherein the guide includes a selective engagement structure proximate the second end of the guide.

7. The system of claim 6, wherein the selective engagement structure includes a threaded region.

8. The system of claim 1, wherein the guide includes an abutment structure that locally increases the diameter of the guide.

9. The system of claim 8, wherein the abutment structure has a diameter greater than the diameter of the channel in the plug.

10. The system of claim 9, wherein the abutment surface has a diameter less than diameter of the bore in the sleeve.

11. The system of claim 1, wherein the prosthetic component is selected from the group consisting of a femoral stem and a trial component.

12. The system of claim 1, further comprising a seal that defines an aperture that is approximately the same diameter as the bore of the sleeve.

13. The system of claim 12, wherein the seal is rigid.

14. The system of claim 12, wherein the seal is disk shaped and the aperture is defined through the center of the seal.

15. The system of claim 12, wherein at least a portion of the seal is flexible.

16. The system of claim 12, wherein the seal is flexible.

17. The system of claim 1, wherein upon being received within the bore of the sleeve, the plug is substantially coextensive with the sleeve.

18. A prosthetic joint system comprising:
   a sleeve having a first end, a second end, and a bore extending between the first and second ends;
   a plug having a first end, a second end, and a channel extending between the first and second ends, wherein the plug is dimensioned to be slidably received within the bore of the sleeve;
   a guide having a first end and a second end, wherein the guide is slidably receivable within the channel of the plug;
   a seal that defines an aperture that is approximately the same diameter as the bore of the sleeve; and a pilot shaft engageable with the guide.

19. The system of claim 18, wherein the pilot shaft is an elongate member having a diameter that is less than the diameter of the bore of the sleeve.

20. A prosthetic joint system comprising:
   a sleeve having a first end, a second end, and a bore extending between the first and second ends;
   a plug having a first end, a second end, and a channel extending between the first and second ends, wherein the plug is dimensioned to be slidably received within the bore of the sleeve;
   a guide having a first end and a second end, wherein the guide is slidably receivable within the channel of the plug;
   wherein the guide includes an abutment structure that locally increases the diameter of the guide;
   a seal that defines an aperture having a diameter greater than the diameter of the abutment structure, and a reduced diameter region of the aperture having a diameter less than the diameter of the abutment structure; and
   a pilot shaft engageable with the guide, wherein the pilot shaft is an elongate member having a diameter that is less than the diameter of the reduced diameter region of the aperture.

21. A prosthetic joint system comprising:
   a sleeve having a first end, a second end, and a bore extending between the first and second ends;

a plug having a first end, a second end, and a channel extending between the first and second ends, the plug having a diameter that is less than the diameter of the bore of the sleeve;

a guide including a portion having a diameter that is less than the diameter of the channel of the plug and an abutment structure having a diameter that is greater than the diameter of the channel of the plug; and a seal that defines an aperture having a diameter greater than the diameter of the abutment structure, and a reduced diameter region of the aperture having a diameter less than the diameter of the abutment structure; and a pilot shaft engageable with the guide.

22. The system of claim 21, wherein the pilot shaft is an elongate member having a diameter that is less than the diameter of the bore of the sleeve.

23. The system of claim 21, wherein the bore is wider at the first end of the bore than at the second end of the bore, and wherein the plug is wider at the first end of the plug than at the second end of the plug.

* * * * *